United States Patent [19]

Lacoste et al.

[11] Patent Number: 5,178,148
[45] Date of Patent: Jan. 12, 1993

[54] METHOD OF AUTOMATICALLY MEASURING THE VOLUME OF A TUMOR OR OF A GLAND, IN PARTICULAR THE PROSTATE, A MEASURING DEVICE, AND A METHOD AND APPARATUS CONSTITUTING AND APPLICATION THEREOF

[75] Inventors: Francois Lacoste, Lyons; Marian Devonec, Miribel; Muriel Cathaud, Venissieux, all of France

[73] Assignee: Technomed International, Paris, France

[21] Appl. No.: 679,863

[22] Filed: Apr. 3, 1991

[30] Foreign Application Priority Data

Apr. 6, 1990 [FR] France .................. 90 04441

[51] Int. Cl.⁵ ............................................. A61B 10/00
[52] U.S. Cl. .................. 128/660.03; 128/660.07; 128/662.06; 128/660.02
[58] Field of Search .............. 128/660.01, 660.03, 128/660.06, 660.07, 660.08, 662.06, 660.02

[56] References Cited

U.S. PATENT DOCUMENTS

| | | | |
|---|---|---|---|
| 4,649,927 | 3/1987 | Fehr et al. | 128/660.07 |
| 4,664,124 | 5/1987 | Ingle et al. | 128/660.02 |
| 4,756,313 | 7/1988 | Terwilliger | 128/662.06 |
| 4,817,616 | 4/1989 | Goldstein | 128/662.06 |
| 4,855,911 | 8/1989 | Lele et al. | 128/660.07 |
| 4,856,528 | 8/1989 | Yang et al. | 128/653 |

OTHER PUBLICATIONS

Watanabe, A Method For volume Estimation by Using Vector Areas and Centroids of Serial Cross-Sections; IEEE Transactions on Biomedical Engineering, vol. BME-29, No. 3, pp. 202-205.

Tamura et al. Pattern Recognition, vol. 20, No. 2 (1987), "3-D Reconstruction for Orthogonal 2-D Echocardiography . . . " pp. 155-162.

Wessels et al. Medical Progress Through Technology, vol. 6, No. 2 (1979) "Recognition of the Pattern in Ultrasonic . . . " pp. 65-72.

Copy of French Search Report.

Primary Examiner—Kyle L. Howell
Assistant Examiner—George Manuel
Attorney, Agent, or Firm—Cohen, Pontani, Lieberman & Pavane

[57] ABSTRACT

The invention relates to a measuring method for automatically measuring the volume of a tumor or of a gland, and also to a measuring device. The measuring device comprises an endocavitary detector probe, in particular a transrectal probe, display means, the display means including an image-forming screen forming images of the tumor or of the gland as provided by the probe, outline-marking means for marking the outline of the image of the tumor or of the gland on the image-forming screen, thereby enabling a marked outline to be obtained, computer means for calculating the volume of the tumor or of the gland on the basis of the marked outline, and optional means for storing the marked outline. The invention makes it very easy for a practitioner to determine the volume of a tumor or of a gland to be treated.

32 Claims, 5 Drawing Sheets

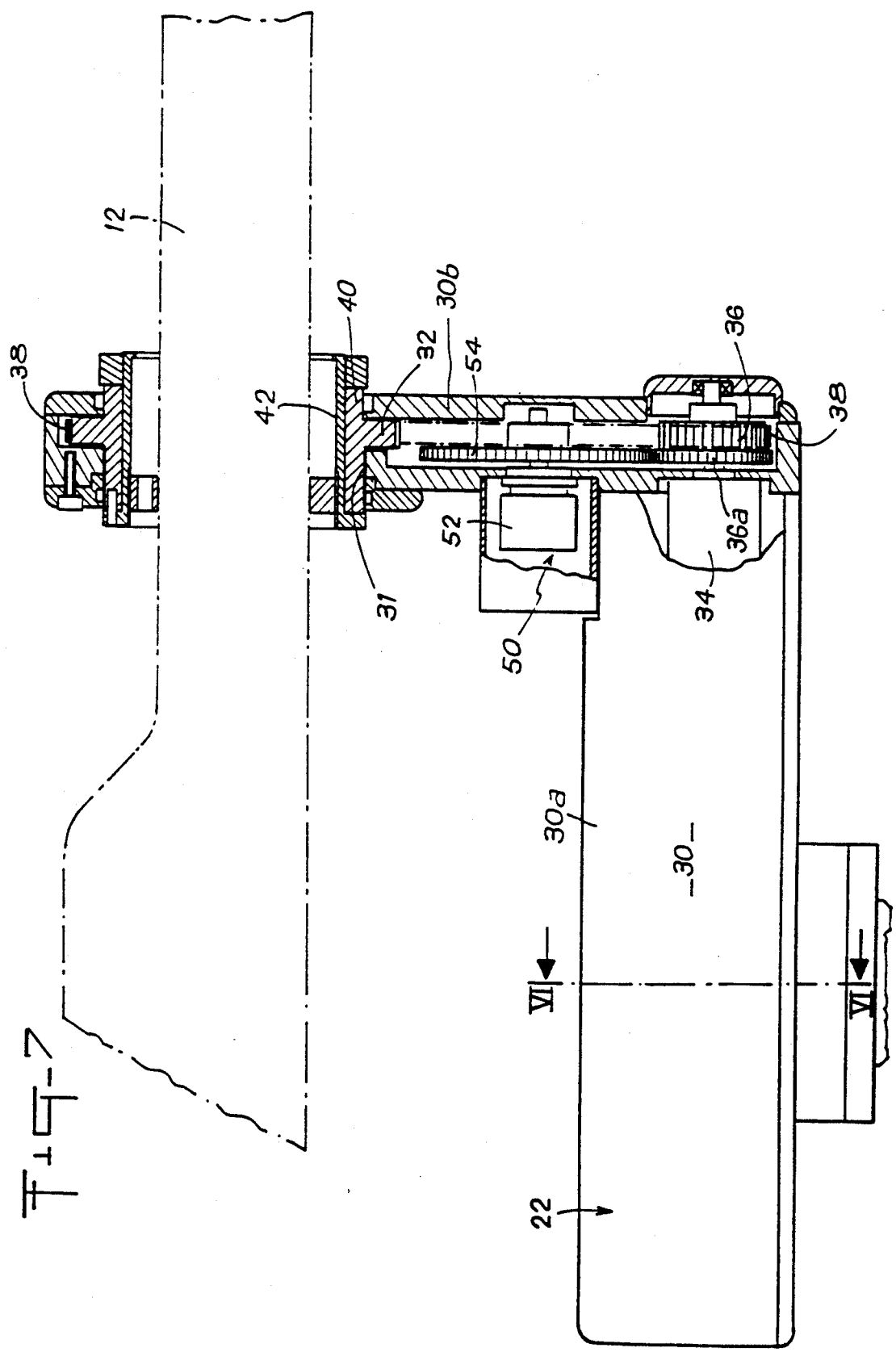

METHOD OF AUTOMATICALLY MEASURING THE VOLUME OF A TUMOR OR OF A GLAND, IN PARTICULAR THE PROSTATE, A MEASURING DEVICE, AND A METHOD AND APPARATUS CONSTITUTING AND APPLICATION THEREOF

The present invention relates essentially to a method of automatically measuring the volume of a tumor or of a gland, in particular the prostate, to a device, and to a method and an apparatus constituting an application thereof.

BACKGROUND OF THE INVENTION

Until now, a practitioner seeking to determine the volume of a tumor, and in particular a tumor of the prostate, has had to proceed with an empirical estimation of this volume by manually displacing a detection probe or "sound" connected to display means including a screen for forming images, with size being evaluated by observing the images formed on the screen. In other words, the practitioner has not had means available for automatically calculating or measuring the volume of a tumor.

An object of the present invention is thus to solve the novel technical problem consisting in providing a solution for automatically calculating or measuring the volume of a tumor or of a gland, in particular a tumor of the prostate or the gland constituted by the prostate, and to do this in a manner which is simple, easy to implement, cheap, and reliable.

Another object of the present invention is to solve the novel technical problem consisting in providing a solution for automatically calculating or measuring the volume of a tumor or a gland, in particular a tumor of the prostate or the gland constituted by the prostate, suitable for use with any type of detector probe, thus making it possible to make use of the detector probes that are already available to the practitioner.

Another object of the present invention is to solve the novel technical problems specified above in a manner which is particularly simple and reliable, by automatically displacing the probe, in particular stepwise, in rotation and/or in translation with synchronized acquisition of image or sections provided by the detector probe.

All of these technical problems are solved for the first time simultaneously and in a manner which is particularly simple by the present invention.

SUMMARY OF THE INVENTION

Thus, in a first aspect, the present invention provides a measuring method for automatically measuring the volume of a tumor or of a gland, in particular a tumor of the prostate or a gland constituted by the prostate, the method comprising the following steps:

providing an endocavitary detector probe and in particular a transrectal probe; display means comprising an image-forming screen for forming images of said tumor or of the gland as provided by the probe; outline-marking means for marking the outline of the tumor or of the gland on an image thereof, e.g. on said image-forming screen, thereby obtaining a marked outline; and computer means for calculating the volume of the tumor or of the gland or the basis of the marked outline;

disposing the detector probe relative to the tumor or to the gland in a position suitable for detecting the tumor or the gland;

putting the probe into operation to provide an image of the tumor or of the gland, e.g. on the screen;

marking the outline of the tumor or of the gland on said image; and calculating the volume of the tumor or of the gland on the basis of the marked outline.

In an advantageous implementaton of the measuring method of the invention, the tumor or the gland is constituted by a tumor of the prostate or by the prostate itself, and the above-mentioned probe is preferably a transrectal probe which is inserted via the rectum to a position suitable for displaying said tumor or said gland by displaying the prostate.

In a more preferred implementation, the probe is initially positioned relative to the apex of the prostate, and an image of the prostate is provided starting from said position.

In another advantageous implementation, said image and/or said marked outline is/are recorded by means for recording the image and/or said outline.

In an advantageous implementation of the measuring method of the invention, the probe is displaced step-by-step from the initial position of the probe until it reaches the position of the neck of the prostate, each image or each outline obtained at each position is recorded, and a mean value for the volume of the prostate is calculated.

In yet another advantageous implementation of the invention, the outline of the tumor or of the gland is marked on an image reproduced from a recording of said image on the recording means, e.g. on a video recorder or on a computer floppy disk.

In yet another advantageous implementation of the method of the invention, the probe is displaced step-by-step in translation or in rotation or simultaneously in translation and in rotation, respectively to obtain radial sections or longitudinal sections or both radial sections and longitudinal sections, and simultaneously the outline of the image of the tumor or of the gland is recorded for each section for which a mean value of the volume of the prostate is calculated.

In another preferred implementation of the method of the invention, the volume of the prostate is calculated from a known mathematical formula given in the literature, for example in the article by Watanabe entitled "A method for volume estimation using vector areas on centroids of serial cross-sections" published in the Journal IEEE Transactions on Biomedical Engineering, Volume BME 29, No. 3, pp. 202–205.

In a second aspect, the present invention also provides a measuring device for measuring the volume of a tumor or of a gland, in particular a tumor of the prostate, or a gland constituted by the prostate, the device comprising a detector probe, display means including an image-forming screen for forming images of said tumor or of said gland as provided by the probe, outline-marking means for marking the outline of the tumor or of the gland on an image thereof, in particular on said image-forming screen, thereby obtaining a marked outline, and computer means for calculating the volume of the tumor or of the gland on the basis of the marked outline, optionally together with means for recording the marked outline and/or the image.

In an advantageous embodiment, the measuring device includes displacement means for displacing the above-mentioned probe step-by-step, the displacement means being selected from rotary displacement means, and means for displacement in axial translation, for obtaining longitudinal sections or radial sections, or both longitudinal and radial sections simultaneously.

In another preferred embodiment, the measuring device of the invention includes a computer for performing the above-mentioned calculation, such as a computer or a microcomputer, said computer including read/write memory, and means for storing the acquired data, e.g. comprising at least one floppy disk. Preferably, the computer also controls the step-by-step displacement of the probe displacement means.

The above-mentioned computer preferably includes image display means independent of the display means of the probe, said computer including means for coupling to the video signal of the detector probe.

In another preferred variant embodiment of the measuring device of the invention, the above-mentioned storage means are suitable for recording the video image received from the detector probe.

In another particular variant of the invention, the endocavitary detector probe is mounted to move in translation and/or in rotation at the end of a positioning device comprising two hinged arms including at least three hinges, and provided with means for locking the hinges simultaneously.

In another variant, the measuring device of the invention includes translation and/or rotation measuring means to measure the value of the displacement in translation and/or rotation of the probe, and said value is used in performing the calculation of the volume of the tumor or of the gland.

In a third aspect, the invention also provides a method of manufacturing apparatus suitable for performing therapeutic treatment, in particular hyperthermia treatment, of a tumor or of a gland, in particular a tumor of the prostate or the gland being the prostate, the method making use of a measuring device for measuring the volume of the tumor or the gland, in particular the prostate, together with integration means for integrating the measured volume of the tumor or of the gland to define parameters for the treatment of said tumor or said gland, which parameters are transmitted to the means for treating the tumor or the gland, said integration means comprising, in particular, a computer, and the above-mentioned measuring device advantageously including a detector probe.

In a fourth aspect, the present invention provides apparatus for performing therapeutic treatment, in particular hyperthermia treatment, of a tumor or of a gland, in particular a tumor of the prostate or the gland being constituted by the prostate the apparatus comprising a measuring device for measuring the volume of the tumor or of the gland, in particular the prostate, together with integration means for integrating the measured volume of the tumor or of the gland to define treatment paremeters to said tumor or of said gland, said integration means including, in particular, a computer. Advantageously, the apparatus includes displacement means for displacing the detector probe step-by-step in rotation and/or in axial translation. The displacement means may be controlled by the computer, sychronously with acquisition of images of the tumor, advantageously by means of an endocavitary type detector probe, in particular a transrectal probe.

In yet another aspect, the present invention provides apparatus for performing therapeutic treatment, in particular hyperthermia treatment, of a tumor or of a gland, in particular a tumor of the prostate or the gland being the prostate, wherein the endocavitary probe is mounted at the end of a positioning device comprising means for moving the probe in translation and/or rotation and provided with means for measuring the value of the translation and/or rotation of the probe, such values being transmitted to the integration means to be integrated in the calculation of the volume of the tumor or of the gland.

It will readily be understood that it is possible with the present invention to measure the volume of a tumor or a gland automatically, and in particular a tumor of the prostate or a gland constituted by the prostate.

To do this, the practitioner merely traces the volume outline in each image by means of an electronic pointer, such as a light pen, a mouse, or a digitizing tablet. These outlines are then stored in the memory of the computer and they may be recorded on a floppy disk.

The computer then calculates the volume of the tumor on the basis of the stored outlines. For example, when sections are obtained in parallel planes by displacing the detector probe in axial translation, the area enclosed by each outline is calculated, and then the sum of the areas is calculated and multiplied by the size of the step betweeen sections. When radial sections are used, obtained by rotating the detector probe about its own axis, then the mean value of the tumor volume is calculated from the area enclosed by each outline obtained for each radially-offset longitudinal section.

The invention makes it possible to measure the volume of a tumor automatically because the computer governs the automatic displacement control (e.g. stepper control) as applied to the displacement means for the detector probe, by rotating the probe about its own axis or by moving it in translation along its axis, or by a combination of both, and by automatically synchronizing the acquisition of the sections obtained from the probe in each of its positions.

In the invention it is preferable to use an echographic type detector probe which delivers a video signal that is coupled to the computer. The computer receives this video image which it stores in memory, and optionally on a floppy disk. It is preferable for the computer to include an independent display monitor for displaying the echographic image and for use by the practitioner to mark the outline of the tumor observed in the section. The computer may advantageously be fitted with an image acquisition card constituting an interface beween the received video image coming from the detector probe and the transformation of the image into digital data.

In the invention, it is also advantageous to display geometrical parameters of the prostate and of the tumor. These parameters advantageously comprise its height, its antero-posterior distance, its transverse distance perpendicular to the antero-posterior distance, and the volume per se of the prostate or of the tumor.

The invention can be adapted to any type of echography and serves to provide reliable and safe determination of prostate volume because the detector probe is displaced automatically, which displacement is extremely accurate because of the automatic control applied thereto.

It will thus be understood that the invention makes it possible to obtain all of the above-specified crucial technical advantages in a manner which is particularly simple, safe, and reliable, and suitable for use on an industrial scale.

BRIEF DESCRIPTION OF THE DRAWINGS

The presently preferred embodiment of the invention is described by way of example with reference to the accompanying drawings, in which:

FIG. 5 is a section view on a larger scale showing details of a ball-and-socket type hinge;

FIG. 7 is a section on line VII—VII of FIG. 2.

DETAILED DESCRIPTION

Although the invention is not limited to the embodiment described, that embodiment nevertheless exemplifies all of the characteristics of the invention, and the drawings representing it thus form an integral part of the description.

Figure 1:
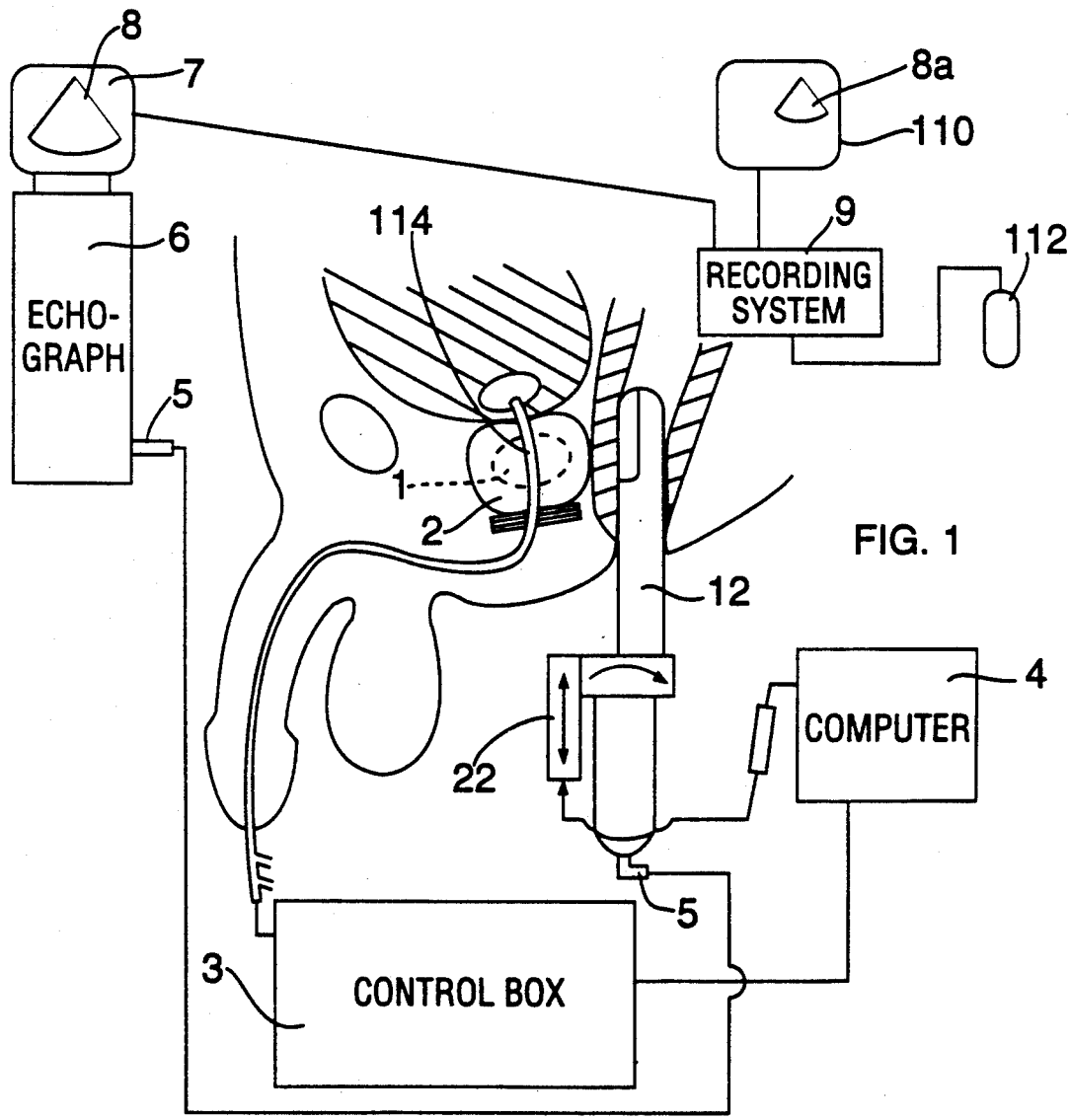
FIG. 1 is a diagram showing the principle on which the presently preferred embodiment of apparatus for therapeutic treatment of a tumor or of a gland, and in particular for hyperthermia treatment of the prostate, is based, the apparatus including a measuring device of the invention for automatically measuring the volume of a tumor or of a gland, and the emitting probe being shown mounted on displacement means and disposed in the tumor-detecting position.

FIG. 1 shows apparatus for therapeutic treatment of a tumor 1 or of a gland 2, in particular a tumor 1 of the prostate 2. For example, this apparatus may comprise a control box 3 provided with computer means 4 such as a computer or a microcomputer, means for measuring the volume of the tumor 1 or of the gland 2 comprising a detector probe 12, and a displacement means 22 for displacing the detector probe 12 and forming a part of a positioning device 10 which is described in greater detail below with reference to FIGS. 2 to 7. The detector probe 12 is preferably an echographic probe and transmits data via an appropriate cable 5 to an echograph 6 which may includes display means 7 such as an image-forming screen 8. According to the invention, it is preferable for the computer 4 to receive the video signal from the echograph 6, in particular via an image acquisition and recording system 9 fitted with an image acquisition card and forming an interface between the video image received from the echograph 6 and transformation of this image into digital data. Such image acquisition cards are commercially available, e.g. from Micromint Inc., 4 Park Street, Vernon Conn., 06066 USA.

It is also preferable for the computer 4 to include independent image display means 110 for displaying images 8a, associated with outline-marking means 112 for marking the outline of the image of the tumor 1 of the gland 2 on the image display screen, said outline-marking means being advantageously electronic, e.g. a mouse (as shown), a light pen, or a digitizing tablet. The means 9 for recording a marked outline are integrated in the present case in the computer 4.

The apparatus advantageously includes treatment means 114 per se for treating the tumor 1 or the gland 2. For example, these treatment means may comprise a microwave-emitting urethral probe for performing therapeutic treatment of the prostate by hyperthermia. By way of example, this probe may be of the type described in French patent application FR-88 15126 which is incorporated herein by reference, or it may be of the type described in the present Applicant's prior patent document FR-900321.

The detector probe 12 is supported by the displacement means 22 which are preferably means for providing stepwise displacement, either in rotation about its own axis or in stepwise translation along said axis, as symbolized by the arrows in FIG. 1. These displacement means 22 are preferably integrated in a positioning device 10 which is described below in greater detail with reference to FIGS. 2 to 7.

Figure 2:
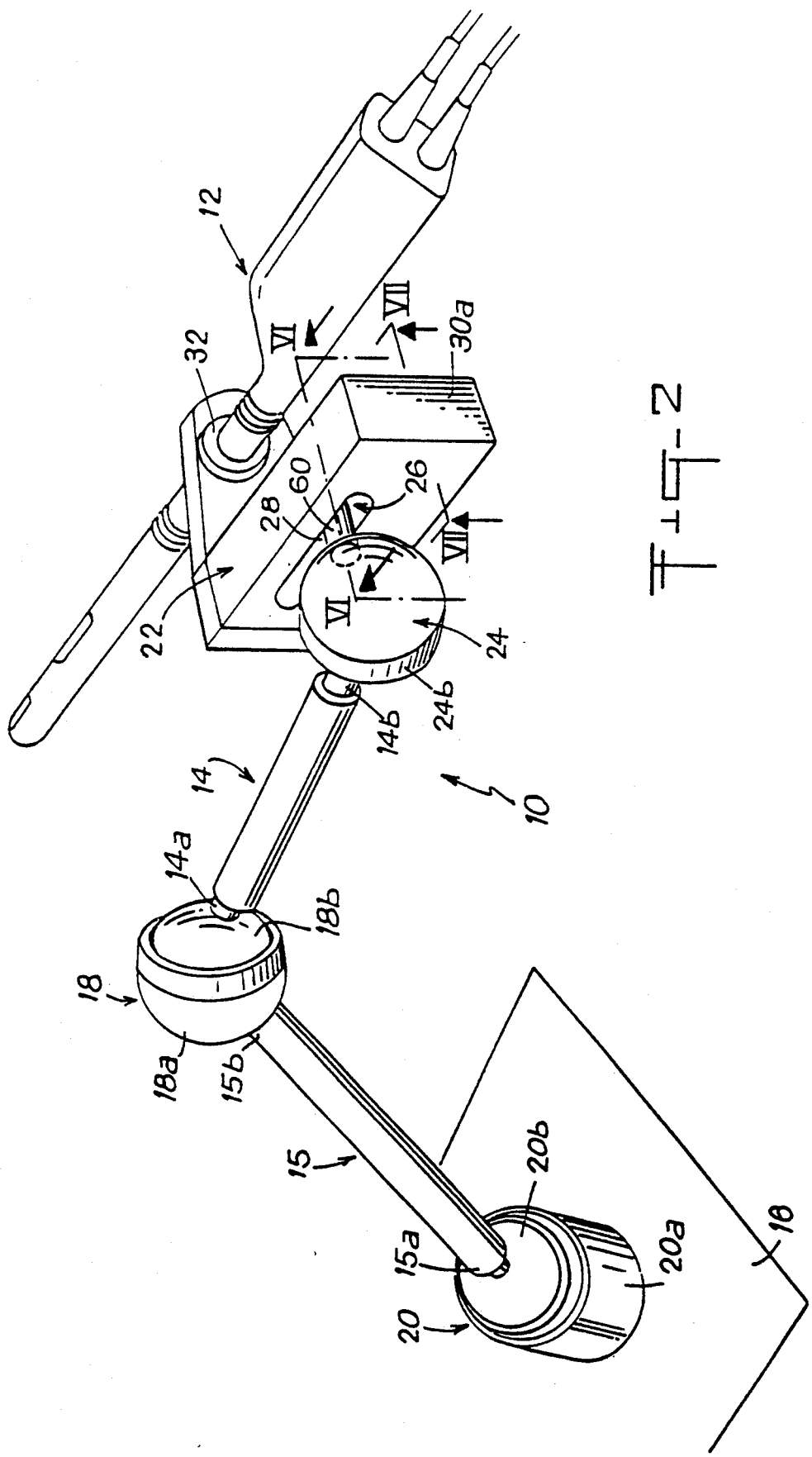
FIG. 2 is a diagrammatic perspective view of means for displacing the detector probe, and including a device for positioning said detector probe in three dimensions.
Figure 3:
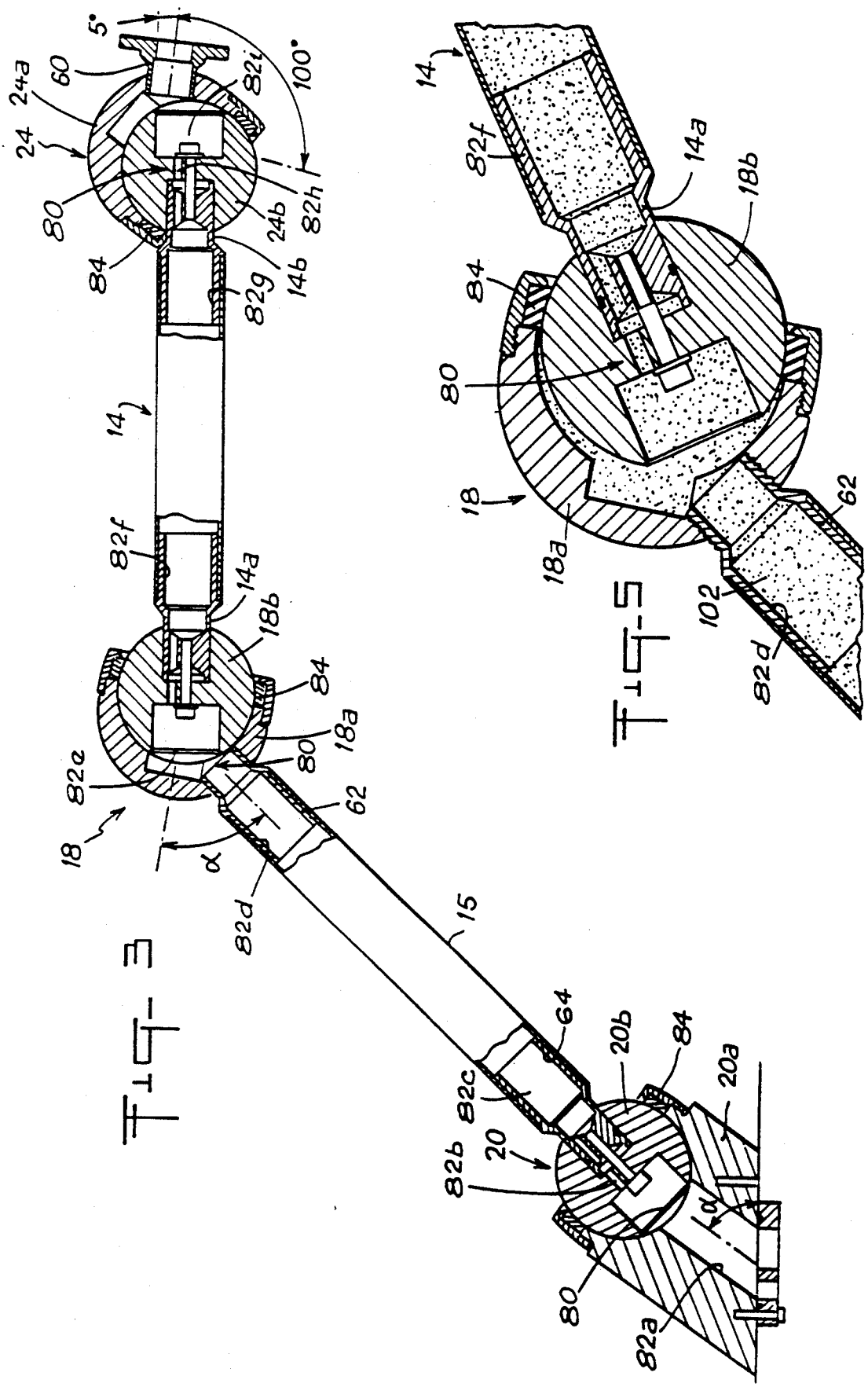
FIG. 3 is a fragmentary longitudinal section showing the ball-and-socket type hinges used in the positioning device of FIG. 2.
Figure 4:
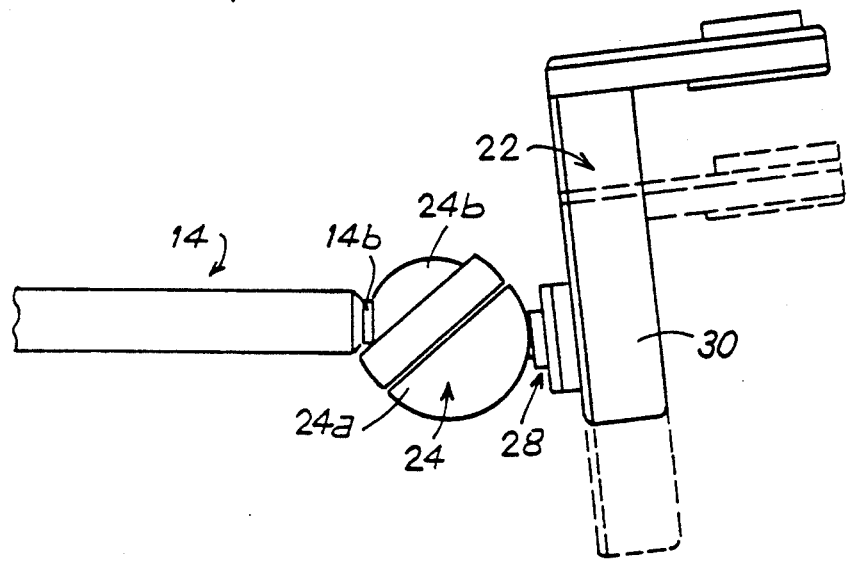
FIG. 4 is a plan view showing the displacement means for displacing the detector probe in axial translation, showing the probe in two diffefent, axially offset positions representing displacement of the probe in translation.

With reference more particularly to FIGS. 2, 3, and 4, a positioning device of the invention for providing positioning in three dimensions is given an overall reference numeral 10 and serves to position an instrument 12 in three dimensions, the instrument being constituted, for example, by an exploration probe and in particular a probe of the echographic or radiographic type, in particular for use with X-rays. The positioning device 10 comprises an essentially rigid arm 14 having a first end 14a and a second end 14b. The first end 14a is hinged relative to a support stand 16 about at least one hinge axis 18, 20, and preferably via at least two hinge axes (18, 20). In addition, the instrument 12 is mounted on a support 22 which is connected to the second end 14b of the arm 14 via at least one hinge axis 24.

According to the present invention, this positioning device is characterized in that the support 22 for the instrument 12 includes a device 26 for providing motion in translation (shown in greater detail in the section of FIG. 6) and serving to move the instrument 12 in translation relative to the second end 14b of the arm 14.

Figure 6:
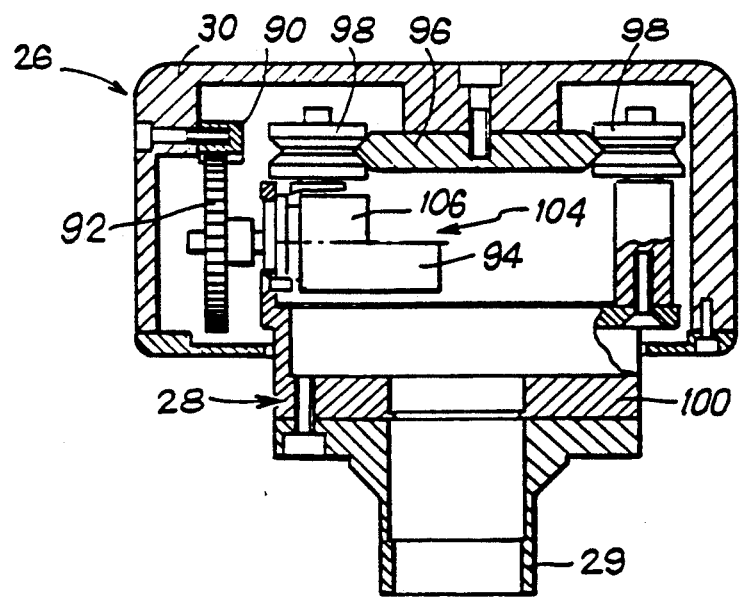
FIG. 6 is a section on line VI—VI of FIG. 2.

In an advantageous embodiment of the invention, this device 26 for providing motion in translation comprises a stationary part 28 fixed to the hinge 24 at the second end 14b of the arm 14 via a link member 29 and a moving part 30 which is movable in translation relative to the stationary part 28, the moving part 30 supporting the instrument 12 (see FIG. 6).

The moving part 30 may be moved in translation relative to the stationary part 28 by any mechanical system well known to the person skilled in the art. For example, the mechanical system may be constituted by a rack system 90 meshing with a pinion 92 on a drive motor 94 mounted on a support piece 100, which is U-shaped for example, and which forms a portion of the stationary part 28. For example, this support piece 100 may also support wheels 98 disposed on either side of a guide rail 96 fixed to the moving part 30, thereby providing accurate guidance of the motion in translation of the moving part 30.

Translation measurement means 104 may also be provided to measure the translation distance of the moving part 30. For example, this translation measurement means may comprise a potentiometer type encoder 106 as is well known to the person skilled in the art.

In a preferred embodiment of the invention, the moving part 30 includes means 32 (more clearly visible in FIG. 7) for rotating the instrument 12 which is shown in dot-dashed lines.

These means 32 for rotating the instrument may, for example, comprises a rotary drive motor 34 acting via a system comprising a toothed wheel 36 co-operating with a drive component 38 such as a toothed belt which rotates a toothed wheel 40. The toothed wheel 40 includes a central orifice 42 coaxial therewith and in which the instrument 12 is inserted, which instrument may be constituted, for example, by a probe for exploration by means of a display, in particular a probe of the ultrasonic type for echographic exploration.

The rotary drive means 32 may include a clutch member for enabling the instrument 12 to be rotated manually. In this case, the clutch member is constituted merely by the toothed belt drive system 38 in combination with the motor 34. It will be understood that when the probe 12 is rotated manually, then the wheel 40 supporting the instrument 12 is likewise rotated manually, together with the belt 38 and the drive wheel 36 of the motor 34 in entirely free manner.

According to yet another particularly advantageous embodiment of the device of the invention, the device includes rotation measuring means 50 for measuring the rotary displacement of the means 32, and in particular of the wheel 40. For example, this measurement means 50 may comprise a potentiometer 52 provided with a toothed wheel 54 which also meshes with a toothed wheel 36a constrained to rotate with the wheel 36 of the motor 34, thereby making it possible to calculate the rotary displacement of the wheel 40 and thus of the instrument 12 on the basis of the number of turns through which the wheel 54 rotates, as is well known to the person skilled in the art.

It should be observed that the displacement step sizes in translation and/or rotation obtained by the translation measuring means 104 and the rotation measuring means 50 are used in calculating the volume of the tumor or of the gland using a known mathematical formula, and in particular the formula given in the article by Watanabe, published in the Journal IEEE Transactions on Biomedical Engineering, Vol. BME 29, No. 3, pp. 202-205.

According to another particularly advantageous embodiment of the invention, the moving part 30 is L-shaped as can clearly be seen in FIG. 2 and in FIG. 7, with one branch 38a thereof moving in translation relative to the stationary part 28 and with the other branch 38b thereof supporting the instrument 12. Because of the L-shape, this other branch extends substantially perpendicularly to the branch 30a. This other branch 30b includes a through orifice 31 whose axis is substantially perpendicular to said other branch 30b, and thus substantially parallel to the branch 30a, and the toothed wheel 40 and the instrument 12 are mounted coaxially in said orifice 31. It will thus be understood that the axis of rotation of the instrument 12 is parallel to the branch 30a, and this constitutes an advantageous structural characteristic of the invention.

According to another presently preferred feature of the positioning device of the invention, at least some of the hinges 18, 20, and 24 are of the ball-and-socket type. In this case, all of the hinges 18, 20, and 24 are of the ball-and-socket type.

In a particular embodiment, as shown, the hinge 24 at the second end 14b of the arm 14 is of the opposite way round to the hinge 18 at the first end 14a of the arm. In the preferred embodiment where all of the hinges 18, 20, and 24 are of the ball-and-socket type, these hinges comprise respectively a stationary part or "socket" (respectively referenced 18a, 20a, and 24a) which is essentially in the form of a truncated sphere, together with a moving part or "ball" which is essentially spherical in shape (and respectively referenced 18b, 20b, and 24b), with the part 24b being clearly visible in FIG. 4.

Since the hinge 24 at the second end 14b of the arm 14 is the opposite way round, its socket 24a is its moving part and supports the stationary part 28 of the device 22 for motion in translation which is fixed thereto by a link member 60.

According to another particularly advantageous characteristic of the invention, the ball-and-socket type hinges 18, 20, 24 are designed in such a manner that the link member such as 60, 62, or 64 in each socket respectively referenced 24a, 28a, or 20a takes up an acute angle of inclination α relative to the axis of symmetry of the fixed part. This angle of inclination α may be different for hinge axis 24 at the second end 14b of the arm 14.

Advantageously, this angle of inclination α lies in the range 20° to 65°, and more preferably in the range 35° to 65°. A particularly preferred angle of inclination is about 55°, as shown.

According to another advantageous characteristic of the invention, a second arm 15 is provided, with the positioning device then comprising a total of not less than three hinges 18, 20, and 24, as shown. The first end 15a of the second arm 15 may be connected to the hinge 20, and the second end 15b may be connected to the hinge 18 which it has in common with the first arm 14.

Because of this structure, a particularly simple positioning device is obtained providing a maximum degree of freedom and in which the instrument 12 is movably mounted by means of the displacement device 22.

In addition, locking means 80 may be provided for locking the hinges 18, 20, and 24 in position. These locking means 80 provide temporary locking by relative displacement between the stationary and the moving parts of the hinges and they are, in particular, of the pneumatic or of the hydraulic type. The locking means 80 constitute an invention independent from the positioning device and they are claimed for themselves.

In a particularly advantageous embodiment, the locking means 80 comprise at least one continuous inside passage 82a to 82i enabling a pneumatic or a hydraulic fluid to pass inside the positioning device 10, with the arms 14 and 15 then being constituted by tubes. The fluid is put under pressure when locking is activated. The pneumatic or hydraulic fluid is naturally conveyed by conventional feed means (not shown).

These feed means preferably feed the pneumatic or hydraulic fluid under pressure 102, which pressure preferably lies in the range 4 bars to 7 bars.

A sealing ring 84 may advantageously be provided towards the free end of each socket 18a, 20a, 24a of each of hinge 18, 20, 24, thereby also providing friction between the stationary and the moving parts of the hinges.

To do this, a sealing ring 84 may be made of a material which is different in nature from the material used for the moving parts of the hinge, thereby increasing friction. For example, sealing ring 84 may be made of PVC while the balls such as 18b, 20b, and 24b is made of a plastic material such as an acetal resin, e.g. polyoxymethylene (POM).

It will thus readily be understood that the complete structure as shown in FIGS. 2 to 7 constitutes an integral part of the invention and therefore forms an integral part of the present description.

It will thus be understood that the invention can be used with various different types of detector probes, in particular various different types of echographic probes and various different types of transrectal probes. Most echographs provide access to the image they display via a TV type video signal output.

The computer 4 may be of the personal computer type, for example. Personal computers of this type are commonly fitted with a "VGA" standard screen.

Because of this standard, it is possible to display the echographic images on the ordinary computer screen.

The displacement means 22 of the detector probe 12 provides motorized displacement for the detector probe 12. The detector probe is preferably a transrectal probe. For strip type detection probes, the displacement is by angular steps. For sector type detector probes the displacement is by axial translation.

The computer 4 is advantageously provided with software for acquiring and storing outlines, for calculating volumes on the basis of such outlines, and for displaying the prostate and the image of the tumor on its video screen. The following operations are programmed in software, namely: waiting for probe installation; rapid scanning of the entire prostate by the translation means; positioning the translation means; acquiring outlines by using outline-marking means 112 such as a mouse, together with values of translation and/or rotation obtained from the translation measuring means 104 and the rotation measuring means 50; storing the outlines and the displacement values in translation and/or rotation on storage means such as a hard disk; calculating the volume of the tumor on the basis of the stored outlines and of the stored values for displacement in translation and/or rotation; displaying the tumor in three dimensions; and displaying tumor parameters.

The invention is equally applicable for automatically acquiring the volume and/or the position of a gland, in particular the prostate.

It will thus be understood that the invention makes it possible to implement the above-described measuring method and also the above-described method of therapeutic treatment.

In practice, the practitioner installs the detector probe 12 in the patient's rectum, with the probe connected to the motorized displacement means 22.

The practitioner then verifies that the detector probe 12 is properly installed and that the entire prostate 2 can be displayed by displacing the probe rapidly using the displacement means 22.

The practitioner then disposes the detector probe 12 at the apex of the prostate 2, and then launches automatic step-by-step displacement of the probe 12 accompanied by simultaneous acquisition and recording of images, with these operations being governed automatically by the computer 4. An image is acquired and recorded for each position of the translation means, and it is recorded in association with values for the displacement in translation and/or rotation of the translation means as provided by the translation measuring means 104 and the rotation measuring means 50. This starting instruction from the practitioner is generally provided by means of a manual pushbutton or switch under computer control.

The practitioner then draws the outlines of the prostate tumor 1, and possibly also of the prostate 2, on the image reproduced on the computer screen 110 by using the outline-marking means 112, which means are advantageously electronic, e.g. a light pencil, a mouse (as shown), or a digitizing tablet. The computer 4 records the outlines as drawn together with the measured values of translation and/or rotation as obtained from the translation measurement means 104 and the rotation measurement means 50. Each position of the detector probe 112 corresponds to a particular outline.

The computer then calculates the mean volume of the tumor 1 and/or of the prostate 2 on the basis of the acquired outline and on the basis of the measured displacement values of the probe 12 in translation and/or rotation.

Thereafter, the computer 4 displays a three-dimensional image of the tumor on the screen 110, together with the geometrical parameters and the mean volumes of the tumor and/or of the gland 2 (in this case the prostate) if so desired.

We claim:

1. A method for measuring the volume of a tumor or of a gland, in particular, the prostate gland or a tumor located therein, the method comprising:
    disposing an endocavitary detector probe relative to the tumor or to the gland in a position suitable for detecting the tumor or the gland, said probe generating a signal representing an image of the tumor or gland detected thereby;
    connecting said signal to an image-forming screen to provide an image of the tumor or of the gland on said image-forming screen;
    moving the probe to a plurality of positions by step-by-step translation and rotation to obtain radial and/or longitudinal sections of the tumor or gland;
    marking the outline of the tumor or of the gland on said image on said image-forming screen for at least a plurality of probe positions; and
    calculating the volume of the tumor or of the gland on the basis of the marked outlines.

2. A method according to claim 1, wherein the tumor or the gland is constituted by a tumor of the prostate or by the prostate itself, and said probe is preferably a transrectal probe, and wherein said disposing step comprises inserting the probe into the rectum to a position suitable for displaying said tumor or said gland.

3. A method according to claim 2, wherein an image of the prostate is provided by positioning the probe in an initial position relative to the apex of the prostate, and then moving the probe relative thereto.

4. A method according to claim 3, wherein said moving step comprises moving the probe in a step-by-step manner from the initial position of the probe until the probe reaches the neck of the prostate, and wherein each image or each outline obtained at each position is recorded and a mean value for the volume of the prostate is calculated.

5. A method according to claim 1, wherein recording means are used to record said image and/or said marked outline.

6. A method according to claim 1, wherein the outline of the tumor or of the gland is marked on an image reproduced from a recording of said image onto the recording means.

7. A method according to claim 1, wherein the outline of the image of the tumor or of the gland is recorded for each probe position.

8. A device for measuring the volume of a tumor or of a gland, in particular a tumor of the prostate, or a gland constituted by the prostate, wherein the device comprises a detector probe generating a signal representing an image of the tumor or gland detected thereby, display means including an image-forming screen connected to said detector probe for forming images of said tumor or of said gland on said image forming screen, means for marking the outline of the tumor or of the gland on an image formed on said image forming screen, and computer means for calculating the volume of the tumor or of the gland from the dimensions of the outline thereof as marked on at least a plurality of said images of the marked outline, optionally together with means for recording the marked outline and/or the image.

9. A measuring device according to claim 8, including displacement means for displacing said probe step-by-step, the displacement means being selected from rotary displacement means, and means for displacement in axial translation.

10. A measuring device according to claim 8, wherein said computer means comprises means for calculating the volume of at least a plurality of the marked outlines, said computer including read/write memory, and means for storing the acquired data.

11. A device according to claim 10, wherein the computer controls the step-by-step displacement of the probe displacement means.

12. A device according to claim 10, wherein said signal comprises a video signal and said computer means includes image display means independent of the image-forming screen, said computer display means including means for coupling to the video signal of the detector probe.

13. A device according to claim 8, wherein the detector probe is a transrectal probe for obtaining images of the prostate by echography.

14. A device according to claim 8, wherein said detector probe is mounted to move in translation and in rotation at the end of a positioning device comprising two hinged arms including at least three hinges, and provided with means for locking the hinges simultaneously.

15. A device according to claim 14, including translation and/or rotation measuring means to measure the value of the displacement in translation and/or rotation of the probe, and wherein said value is used in performing the calculation of the volume of the tumor or of the gland.

16. The device according to claim 8, further comprising integration means for integrating the measured volume of the tumor or of the gland to define treatment parameters of said tumor or of said gland and transmitting means to transmit said treatment parameters to a means for treating the tumor or the gland, said integration means including, in particular, a computer.

17. Apparatus according to claim 16, including displacement means for displacing the detector probe step-by-step in rotation and/or in axial translation.

18. Apparatus according to claim 17, wherein the displacement means are controlled by a computer synchronously with the acquisition of images of the tumor or of the gland.

19. Apparatus according to claim 18, further comprising an endocavitary probe mounted at the end of a positioning device comprising means for moving the probe in translation and/or rotation and provided with means for measuring the value of the translation and/or rotation of the probe, such values being transmitted to the integration means to be integrated in the calculation of the volume of the tumor or of the gland.

20. The device according to claim 8, further comprising means for recording at least a plurality of the marked outlines and/or the images formed on the image-forming screen.

21. Apparatus for the therapeutic treatment of a tumor, comprising:
a device for therapeutically treating said tumor;
display means comprising:
(i) exploratory probe means generating a signal corresponding to an image;
(ii) an image-forming screen for forming images generated by said probe;
means for displacing said probe to a plurality of positions by step-by-step translation and rotation to obtain radial and/or longitudinal sections of said tumor;
means for marking the outline of the tumor on the images on said image-forming screen for at least a plurality of positions of said probe;
computer means for calculating the volume of the tumor on the basis of the marked outlines and integrating the calculated volume measurements to define the treatment parameters of the tumor; and
transmitting means for transmitting said parameters to said device for treating the tumor.

22. The apparatus according to claim 21, wherein said displacing means are controlled by said computer means synchronously with the acquisition of images of the tumor.

23. Apparatus according to claim 21, wherein said probe is mounted at the end of a positioning device comprising said displacement means and provided with means for measuring the value of the translation and/or rotation of said probe, said values being transmitted to the integration means to be integrated for the calculation of the volume of the tumor.

24. Apparatus according to claim 21, wherein said computer means comprise a computer or a micro-computer including a read/write memory and means for storing the acquired data.

25. Apparatus according to claim 21, wherein said computer includes image display means independent of the image-forming screen.

26. Apparatus according to claim 21, wherein the detector probe is an endorectal probe for displaying the prostate.

27. Apparatus according to claim 23, wherein the positioning device comprises two hinged arms including at least three hinges, and provided with means for locking the hinges simultaneously.

28. Apparatus according to claim 22, wherein said probe is mounted at the end of a positioning device comprising said displacing means and provided with means for measuring the value of the translation and/or rotation of said probe, said values being transmitted to the integration means to be integrated for the calculation of the volume of the tumor.

29. Apparatus according to claim 28, wherein said computer means comprises a computer or a micro-computer including a read/write memory and means for storing the acquired data.

30. Apparatus according to claim 29, wherein said computer includes image display means independent of the image-forming screen.

31. Apparatus according to claim 29, wherein the detector probe is an endorectal probe for displaying the prostate.

32. Apparatus according to claim 31, wherein the positioning device comprises two hinged arms including at least three hinges, and provided with means for locking the hinges simultaneously.

* * * * *